United States Patent
Deshpande et al.

(10) Patent No.: US 7,214,837 B2
(45) Date of Patent: May 8, 2007

(54) PROCESS FOR PREPARATION OF A MIXTURE OF ALCOHOLS AND KETONES BY LIQUID PHASE OXIDATION OF HIGHER ALKANES

(75) Inventors: Raj Madhukar Deshpande, Maharashtra (IN); Vilas Hari Rane, Maharashtra (IN); Raghunath Vitthal Chaudhari, Maharashtra (IN)

(73) Assignee: Council of Scientific and Industrial Research (IN)

( * ) Notice: Subject to any disclaimer, the term of this patent is extended or adjusted under 35 U.S.C. 154(b) by 401 days.

(21) Appl. No.: 10/976,737

(22) Filed: Oct. 29, 2004

(65) Prior Publication Data

US 2006/0094905 A1 May 4, 2006

(51) Int. Cl.
*C07B 41/02* (2006.01)
*C07C 27/16* (2006.01)

(52) U.S. Cl. ............... 568/910.5; 568/910; 568/909.8; 568/338; 568/342; 568/346; 568/385

(58) Field of Classification Search ............. 568/910.5, 568/910, 909.8, 338, 342, 346, 385
See application file for complete search history.

(56) References Cited

U.S. PATENT DOCUMENTS 4,459,427 A * 7/1984 Middleton et al. .......... 568/342
4,978,800 A * 12/1990 Sanderson et al. .......... 568/385

* cited by examiner

*Primary Examiner*—Elvis O. Price
(74) *Attorney, Agent, or Firm*—Ostrolenk, Faber, Gerb & Soffen, LLP

(57) ABSTRACT

The present invention provides a process for the production of a mixture of alcohols and ketones by the liquid phase oxidation of higher alkanes using a catalyst system consisting of transition group metal such as palladium and support such as alumina, silica, carbon, preferably carbon in the presence of alkyl hydroperoxide as oxygen carrier, under stirring conditions at a temperature range of 10°–120° C. and at atmospheric pressure in a stirred glass reactor for a period of 1–30 h. The present invention produces a mixture of alcohols and ketones with high selectivity (preferably 60–90%) along with other byproducts such as diketones and acids.

14 Claims, No Drawings

PROCESS FOR PREPARATION OF A MIXTURE OF ALCOHOLS AND KETONES BY LIQUID PHASE OXIDATION OF HIGHER ALKANES

FIELD OF INVENTION

The present invention relates to a process for the preparation of mixture of alcohols and ketones by liquid phase oxidation of higher alkanes. More particularly the present invention relates to a process for the manufacture of a mixture of alcohols and ketones by liquid phase oxidation of higher alkanes using alkyl hydroperoxide as the oxygen donor in presence of supported palladium catalysts.

BACKGROUND OF THE INVENTION

The n-alkanes are an important feedstock for manufacture of numerous intermediates and finished products, such as alcohols and ketones, having tremendous demand in the manufacture of variety of industrially important products. The alcohols and ketones are either sulfonated or ethoxylated to different types of detergents. Fatty alcohols and their derivatives are of great commercial importance as surfactants, plasticizers, etc. The most widely used are $C_{12}$–$C_{16}$ fatty alcohols. A number of studies have been reported in the literature on the oxidations of higher alkanes to alcohols and ketones via air or oxygen as an oxidant. Reactions of alkanes with alkyl hydroperoxide for the manufacture of alcohols and ketones have also been extensively studied in the literature.

The use of palladium metal and palladium organometallic complexes for alkane oxidation are well known. A majority of literature reports on palladium catalyzed oxidation deal oxidation of with lower alkane oxidation ranging from methane to butane using molecular oxygen, in a highly acidic medium. Reference is made to Rudakov et al, Metallokompleksnyi Katal., 116–29, 1977 wherein the oxidation of saturated hydrocarbons is reported using palladium(II) complexes as catalysts in highly acidic media like sulfuric acid, sulfuric acid-aluminum sulfate, and phosphoric acid-boron trifluoride. The disadvantage of this system is the essential requirement of a highly acidic medium, to conduct the reaction, which is avoided in the present invention. The present invention can be conducted without any solvent, and hence is avoid of any acidic/corrosive components.

Reference is made to Herron et al, New J. Chem., 13(10–11), 761–6, 1989, wherein zeolite supported Fe/Pd bimetallic catalysts are used for the selective oxidation of alkanes at room temperature. Here a mixture of hydrogen and oxygen, or $H_2O_2$ is used as an oxidant.

U.S. Pat. No. 5,235,117 teaches the preparation of boric acid and its use in the oxidation of saturated hydrocarbons to alcohols is reported. In the present invention the oxidation catalyst used is supported Pd catalyst, which catalyzes the alkane oxidation in the presence of alkyl hydroperoxide. No boric acid is employed in the present invention.

$PdSO_4 \cdot 2H_2O$ is used as a catalyst in International Patent Appl, WO 9214738 A1 to convert methane to $MeOSO_3H$ in 20% oleum at 100° C. The process uses $PdSO_4$ as an oxidation catalyst for oxidation of methane to esters and alcohols in highly acidic medium is also reported. In the present invention, the catalyst used is a supported Pd catalyst and the reaction is carried out in a solvent, free from any acidic components.

A very high alcohol to ketone ratio was reported in the oxidation of cyclohexane with t-butyl hydroperoxide (TBHP) over Fe-tris[2-pyridyl methyl]amine catalyst. The alcohol: ketone ratio was 18, at an alkane conversion of ~30% [J. Kim et. al; J. Mol. Catal, A:Chem., 117, 83, (1997)]. The oxidation of cyclohexane by TBHP in the presence of titanium alkoxide produced the corresponding alcohols and ketones, whereas, other titanium complexes with titanyl or peroxo-titanium groups were not effective [(M Fujiwara et al., J. Mol. Catal. A:Chem., 142, 77 (1999)].

Metal porphyrin catalysts are also reported to be active for the oxidation of isobutane and cumene. In the presence of oxygen these substrates form the hydroperoxide, which then decomposes to yield the alcohol and ketone. The oxidation of n-dodecane with cumene hydroperoxide or TBHP to detergent grade alcohols has been reported using Fe, Mn, Co porphyrin catalysts and mixtures [U.S. Pat. No. 4,978,799]. Metal acetylacetonate complexes are reported to be active for the oxidation of isobutane and cumene. In the presence of oxygen these substrates form the hydroperoxide, which then decomposes to yield the alcohol/ketone products. The productions of detergent grade alcohols by the oxidation of n-dodecane with cumene hydroperoxide or TBHP have been reported using Fe, Ru and Cr acetyacetonate catalysts and their mixture [U.S. Pat. No. 4,978,800]. In the presence of $RuCl_2(PPh_3)_3$, and TBHP, decane oxidation with 28% conversion has been observed. Ketones are the major product formed with 38% selectivity. The alcohol formation is about 2% [S. I. Murahashi, et al., Tetrahedron Lett., 34(8), 1299 (1993)]. U.S. Pat. No. 4,459,427 describes a process for the production of alcohol and ketone derivatives by reacting the linear or branched alkanes ($C_2$–$C_{20}$) with TBHP at ambient or elevated temperature and pressure in the presence of iron or manganese phthalocynine or porphyrin square planar complexes having heterocyclic nitrogen donor ligands, and where the complex has either no axial ligands, e.g. the lower valency or cationic complex, or has an axial ligand which is non-coordinating or weakly-coordinating. D. Mansuy et al. [Angew. Chem. Intl. Ed. Engl., 19 (11), 909 (1980)], describe the hydroxylation of cyclohexane and n-heptane by alkyl hydroperoxide using metalloporphyrin and in particular iron (111) and manganese (111) porphyrins in the form of Fe(tetraphenyl porphyrin)Cl and Mn(TPP)Cl. Ru/C has been used for the oxidation of different alkanes (cycloalkanes, n-heptane and n-decane) using TBHP and peracetic acid as the oxidants, to yield 72–90% of oxygenates (alcohol+ketones) [S. Murahashi, et al., J. Org. Chem., 65, 9186 (2000)].

The oxidation of cyclohexane, hexane and heptane to alcohols and ketones has also been reported using cis-[RU (II)(L)$_2$—(OH$_2$)$_2$]$^{2+}$ complex catalysts (where L=substituted 2,2'-bipyridines of 1,10-phenanthrolines [T. Lau et al., J. Chem. Soc., Chem. Commun., 1406 (1988)].

Numerous heterogeneous catalysts have also been found to be active for the oxidation of alkanes. Co/Mn supported on different microporous aluminophosphates were used for the oxidation of dodecane with air at 100° C. [R Raja and J. M. Thomas, Chem. Commun., (17), 1841 (1998)]. The highest conversion of dodecane reported was 5.5%. The products formed were $C_{12}$ alcohols, ketones and gaseous carbon oxides. The selectivity to alcohol and ketone was 35% and 20%, respectively. The selectivity for terminal alcohol and aldehyde was 37%.

In the literature, a number of researchers have reported that detergent grade alcohols were obtained in high selectivity by the oxidation of higher alkanes using boric acid as a catalyst. A. N. Bashikirov, et al. [Proc. World Pet. Cong., Vol. 4 175 (1959)] have reported the synthesis of higher aliphatic alcohols by liquid phase oxidation of paraffinic hydrocarbons in the presence of boric acid and found that a high selectivity to alcohols can be achieved by proper selection of reaction conditions. Nippon Shokubai in Japan practices a commercial process for the manufacture of detergent alcohols by alkane oxidation in the presence of boric acid [U.S. Pat. No. 3,660,504]. Here the diluted oxygen (5% in nitrogen) is used as the oxygen source and the alkyl hydroperoxides are formed in situ. These interact with the boric acid to form borate esters, which on hydrolysis yield the detergent alcohols. The conversion level for alkane is 31% with a selectivity of 72% to alcohols, No metal catalysts are used in this process. The boric acid serves as an esterification agent in the oxidation, which prevents them from further oxidation by interrupting the oxidative conversion chain at the alcohol stage. A similar observation has been reported by N. J. Stevens and J. R. Livingston "A New Route for Alcohols" [Chem. Eng. Progress, 64(7), 62 (1968)]. M. Iam and M. Hassan [(Ind. Eng. Chem. Prod. Res., 20, 315 (1981)] have reported that the direct oxidation of n-dodecane in the presence of boron compounds like tributoxyboroxine, boron trioxide, dibut4oxyborane, etc. using dilute oxygen (4% $O_2$ in $N_2$) leads to a mixture of the six possible straight-chain $C_{12}$ alcohols.

U.S. Pat. No. 5,767,320 describes a process for the oxidation of cyclohexane to a mixture of cyclohexanone and cyclohexanol using Fe, Co, Cu, Cr, Mn complex of phthalocynine or porphyrin and mixture as catalysts in which some or all of the hydrogen atoms of the phthalocynine or porphyrin have been replaced by electron withdrawing groups.

OBJECTIVES OF THE INVENTION

The main object of the present invention is to provide a process for the preparation of a mixture of alcohols and ketones by the liquid phase oxidation of higher alkanes ($C_8$–$C_{20}$) in the presence of alkyl hydroperoxide as an oxidant using supported palladium catalyst.

Yet another object of the present invention is to develop a process, which will be environmentally more benign.

Yet another object of the invention to provide a process for making mixtures of alcohols and ketones with minimum by-products formation.

Another object of this invention is to use the solid inert support for supporting the transition metal and may be selected from alumina, silica, carbon, preferably carbon.

Yet another object of the present invention is to use the linear alkanes, which may be selected from $C_6$ to $C_{20}$ paraffins, preferably $C_{10}$ to $C_{16}$ paraffins.

Yet another object of this invention is to use the alkyl hydroperoxide as an oxidant, which may be selected from cumene hydroperoxide, t-butyl hydroperoxide, t-amyl hydroperoxide, preferably t-butyl hydroperoxide.

Yet another object of this invention is to provide a process for the production of a mixture of alcohols and ketones at room or ambient temperature and atmospheric pressure conditions.

SUMMARY OF THE INVENTION

The present invention provides a process for the preparation of a mixture of alcohols and ketones by the liquid phase oxidation of higher alkanes using a catalyst system consisting of palladium metal and support such as alumina, silica, carbon, preferably carbon in the presence of an alkyl hydroperoxide as oxidant.

The reactions were carried out at a temperature ranging between 10°–120° C. and at atmospheric pressure in the presence of alkyl hydroperoxide as an oxidant in a stirred glass reactor for a period of 1–30 h. After the reaction was completed, the reaction mixture was cooled to room temperature, filtered and the reactants and products were analyzed by gas chromatograph (GC). The products were also identified by gas chromatograph—mass spectroscopy (GCMS). The present invention produces a mixture of alcohols and ketones with high selectivity (preferably 60–90%) along with other byproducts such as diketones and acids.

Accordingly the present invention provides a process for the preparation of a mixture of alcohols and ketones of higher alkanes selected from the group consisting of $C_8$–$C_{20}$ alkanes comprising subjecting the higher alkanes to liquid phase oxidation using a supported palladium catalyst system in the presence of alkyl hydroperoxide as an oxidant, cooling the reaction mixture to room temperature, and separating the products so obtained.

In one embodiment of the invention, the catalyst support is an inert solid support and is selected from the group consisting of alumina, silica and carbon, preferably carbon.

In another embodiment of the invention, the catalyst contains salts of palladium selected from the group consisting of acetates, bromides, chlorides, hydroxides, iodides, carbonates, nitrates, oxides, sulfides and propionates, preferably nitrates.

In another embodiment of the invention, the concentration of palladium in the catalyst is in the range of 0.3–10% by weight of the support.

In yet another embodiment of the invention, the mole ratio of the higher alkanes to palladium is in the range of 1–5000.

In another embodiment of the invention, the mole ratio of higher alkanes to the alkyl hydroperoxide is in the range of 0.1–5.0.

In another embodiment of the invention, the reaction is carried out at a temperature in the range of 10°–120° C.

In yet another embodiment of the invention, the reaction is conducted at atmospheric pressure in air or inert atmosphere.

In a further embodiment of the invention, the liquid phase oxidation is carried out at a temperature in the range of 10°–120° C. and at atmospheric pressure for a period of 1–30 h.

In another embodiment of the invention, the reaction is carried out in a solvent selected from the group consisting of primary alcohol, alkyl nitrile and dialkyl ketone.

In yet another embodiment of the invention, the alkyl hydroperoxide is used as a solution in primary alcohols, alkanes, dialkyl peroxide or in an aromatic solvent.

In another embodiment of the invention, the products are separated by distillation.

DETAILED DESCRIPTION OF THE INVENTION

Literature reports indicate that homogeneous porphyrin, phthalocynine and similar planar complexes of metal like Fe, Co, Mn, Cu, Ru, Rh are active for the oxidation of alkane in the presence of alkyl hydroperoxide [TBHP, CHP]. There are no reports on the use of heterogeneous palladium metal catalysts for the oxidation of alkanes using alkyl hydroperoxide. These drawbacks are obviated in the present invention, which employs supported Pd catalyst, using alkyl hydroperoxide in the absence of any co-catalyst or any acidic solvent. In fact the present invention can also be practiced in the absence of any solvent.

The present invention provides a process for the preparation of alcohols and ketones by the liquid phase oxidation of higher alkanes using a supported palladium catalyst system in the presence of alkyl hydroperoxide as oxygen carrier at moderate temperatures and atmospheric pressure. This invention provides a process by the use of a heterogeneous catalyst system, which can be separated from the reaction mixture with ease and reused for the reaction and also provides a process that is environmentally more benign.

In the process of the invention, higher alkanes ($C_8$–$C_{20}$) are subjected to liquid phase oxidation to obtain a mixture of alcohols and ketones using a supported palladium catalyst system and in the presence of alkyl hydroperoxide as an oxidant. The reaction is preferably carried out at a temperature in the range of 10°–120° C., at atmospheric pressure and for a period of 1–30 h. The reaction mixture is cooled after oxidation to room temperature and the products obtained are separated by conventional techniques such as distillation.

The support used for the preparation of catalyst is an inert solid support and may be selected from alumina, silica and carbon, preferably carbon. The salts of palladium used in the catalyst are selected from acetates, bromides, chlorides, hydroxides, iodides, carbonates, nitrates, oxides, sulfides, propionates, preferably nitrates. The concentration of palladium in the catalyst is in the range of 0.3–10% of support.

The mole ratio of alkanes to palladium is in the range of 1–5000 and the mole ratio of alkanes to the alkyl hydroperoxide is in the range of 0.1–5.0. The reaction is preferably carried out at a temperature in the range of 10°–120° C. and at atmospheric pressure in air or inert atmosphere. The reaction is preferably carried out in the presence of a solvent such as a primary alcohol, alkyl nitrile or dialkyl ketone.

The alkyl hydroperoxide is used as a solution in primary alcohols, alkanes, dialkyl peroxide or an aromatic solvent.

The process of the invention is described in detail in the following illustrative and non-limitative examples.

EXAMPLE 1

A mixture of 9.913 g TBHP in 6.247 g decane, 0.5 g 5% Pd/C catalyst was charged to the glass reactor of 50 ml capacity fitted with a water condenser. The reaction was carried at 25° C. at atmospheric pressure under constant stirring for a period of 22 hours. The temperature was maintained by the use of circulated high temperature bath. At the end of the reaction, the reaction mixture was cooled to room temperature, filtered to separate the catalyst, and then weighed. The reactants and products were analyzed by gas chromatograph and the products were also identified by gas chromatography mass spectometery. The hydroperoxide in the reaction mixture was estimated by iodometric titration method. The GC analysis of reaction mixture showed 25.1% conversion of n-decane with 41.5% and 8.3% selectivity to decanones and decanols, respectively. Diketones and acids are formed as side products with 13.4% and 3.2% selectivity, respectively.

EXAMPLE 2

A mixture of 9.913 g TBHP in 6.247 g decane, 0.5 g 5% Pd/C catalyst was charged to the glass reactor of 50 ml capacity fitted with a water condenser. The reaction was carried at 80° C. at atmospheric pressure under constant stirring for a period of 6 hours. The temperature was maintained by the use of circulated high temperature bath. At the end of the reaction, the reaction mixture was cooled to room temperature, filtered to separate the catalyst, and then weighed. The reactants and products were analyzed by gas chromatograph and the products were also identified by gas chromatography mass spectometery. The hydroperoxide in the reaction mixture was estimated by iodometric titration method. The reaction was carried at 80° C. with constant stirring for a period of 6 hours. The GC analysis of reaction mixture showed 13.6% conversion of n-decane with 56.6% and 12.9% selectivity to decanones and decanols, respectively. Diketones and acids are formed as side products with 13.2% and 3.5% selectivity, respectively.

EXAMPLE 3

A mixture of 9.913 g TBBP in 6.247 g decane, 0.5 g 5% Pd/C catalyst was charged to the glass reactor of 50 ml capacity fitted with a water condenser. The reaction was carried at 90° C. at atmospheric pressure under constant stirring for a period of 6 hours. The temperature was maintained by the use of circulated high temperature bath. At the end of the reaction, the reaction mixture was cooled to room temperature, filtered to separate the catalyst, and then weighed. The reactants and products were analyzed by gas chromatograph and the products were also identified by gas chromatography mass spectometery. The hydroperoxide in the reaction mixture was estimated by iodometric titration method. The GC analysis of reaction mixture showed 18.7% conversion of n-decane with 54.5% and 10.8% selectivity to decanones, decanols, respectively. Diketones and acids are formed as side products with 11.9% and 2.8% selectivity, respectively.

EXAMPLE 4

A mixture of 9.913 g TBHP in 6.247 g decane, 1.0 g 5% Pd/C catalyst was charged to the glass reactor of 50 ml capacity fitted with a water condenser. The reaction was carried at 80° C. at atmospheric pressure under constant stirring for a period of 6 hours. The temperature was maintained by the use of circulated high temperature bath, At the end of the reaction, the reaction mixture was cooled to room temperature, filtered to separate the catalyst, and then weighed. The reactants and products were analyzed by gas chromatograph and the products were also identified by gas chromatography mass spectometery. The hydroperoxide in the reaction mixture was estimated by iodometric titration method, The GC analysis of reaction mixture showed 20.4% conversion of n-decane with 68.0% and 21.3% selectivity to decanones, decanols, respectively. Diketones and acids are formed as side products with 9.0% and 2.5% selectivity, respectively.

EXAMPLE 5

A mixture of 7.3 g decane, 8.0 g TBBP in di-t-butylperoxide (DTBP), 0.5 g 5% Pd/C catalyst was charged to the glass reactor of 50 ml capacity fitted with a water condenser. The reaction was carried at 80° C. at atmospheric pressure under constant stirring for a period of 6 hours. The temperature was maintained by the use of circulated high temperature bath. At the end of the reaction, the reaction mixture was cooled to room temperature, filtered to separate the catalyst, and then weighed. The reactants and products were analyzed by gas chromatograph and the products were also identified by gas chromatography mass spectometery. The hydroperoxide in the reaction mixture was estimated by iodometric titration method. The GC analysis of reaction mixture showed 25.1% conversion of n-decane with 28.1% and 10.4% selectivity to decanones, decanols, respectively. Diketones and acids are formed as side products with 7.4% and 0.7% selectivity, respectively.

EXAMPLE 6

A mixture of 3.942 g decane, 3.12 g TBRP in di-t-butylperoxide (DTBP), 0.25 g 5% Pd/C and 8.913 g t-butanol was charged to the glass reactor of 50 ml capacity fitted with a water condenser. The reaction was carried at 80° C. at atmospheric pressure under constant siring for a period of 6 hours. The temperature was maintained by the use of circulated high temperature bath. At the end of the reaction, the reaction mixture was cooled to room temperature, filtered to separate the catalyst, and then weighed. The reactants and products were analyzed by gas chromatograph and the products were also identified by gas chromatography mass spectomerty. The hydroperoxide in the reaction mixture was estimated by iodometric titration method. The GC analysis of reaction mixture showed 20.7% conversion of n-decane with 15.4% and 5.9% selectivity to decanones, decanols, respectively. Diketones are formed as side products with 1.5% selectivity.

EXAMPLE 7

A mixture of 3.942 g decane, 2.79 g TBHP in di-t-butylperoxide (DTBP), 0.5 g 5% Pd/C and 9.028 g isopropyl alcohol was charged to the glass reactor of 50 ml capacity fitted with a water condenser. The reaction was carried at 60° C. at atmospheric pressure under constant stirring for a period of 6 hours. The temperature was maintained by the use of circulated high temperature bath. At the end of the reaction, the reaction mixture was cooled to room temperature, filtered to separate the catalyst, and then weighed. The reactants and products were analyzed by gas chromatograph and the products were also identified by gas chromatography mass spectomerty. The hydroperoxide in the reaction mixture was estimated by iodometric titration method. The GC analysis of reaction mixture showed 4.4% conversion of n-decane with 38.1% and 44.0% selectivity to decanones, decanols, respectively. Diketones are formed as side products with 2.0% selectivity.

EXAMPLE 8

A mixture of 5.0 g n-dodecane, 2.981 g TBHP in di-t-butylperoxide (1DTBP), 0.25 g 5% Pd/C catalyst was charged to the glass reactor of 50 ml capacity fitted with a water condenser. The reaction was carried at 25° C. at atmospheric pressure under constant stirring for a period of 6 hours. The temperature was maintained by the use of circulated high temperature bath. At the end of the reaction, the reaction mixture was cooled to room temperature, filtered to separate the catalyst, and then weighed. The reactants and products were analyzed by gas chromatograph and the products were also identified by gas chromatography mass spectomerty. The hydroperoxide in the reaction mixture was estimated by iodometric titration method. The GC analysis of reaction mixture showed 2.3% conversion of n-dodecane with 67.2% and 26.6% selectivity to dodecones, dodecanols, respectively. Diketones are formed as side products with 1.6% selectivity.

EXAMPLE 9

A mixture of 5.0 g n-dodecane, 2.981 g TBHP in di-t-butylperoxide (DTBP), 0.25 g 5% Pd/C catalyst was charged to the glass reactor of 50 ml capacity fitted with a water condenser. The reaction was carried at 45° C. at atmospheric pressure under constant stirring for a period of 6 hours. The temperature was maintained by the use of circulated high temperature bath. At the end of the reaction, the reaction mixture was cooled to room temperature, filtered to separate the catalyst, and then weighed. The reactants and products were analyzed by gas chromatograph and the products were also identified by gas chromatography mass spectomerty. The hydroperoxide in the reaction mixture was estimated by iodometric titration method. The GC analysis of reaction mixture showed 3.9% conversion of n-dodecane with 63.3% and 25.0% selectivity to dodecanones, dodecanols, respectively. Diketones are formed as side products with 5.7% selectivity.

EXAMPLE 10

A mixture of 5.0 g n-dodecane, 2.981 g TBHP in di-t-butylperoxide (DTBP), 0.25 g 5% Pd/C catalyst was charged to the glass reactor of 50 ml capacity fitted with a water condenser. The reaction was carried at 60° C. at atmospheric pressure under constant stirring for a period of 6 hours. The temperature was maintained by the use of circulated high temperature bath. At the end of the reaction, the reaction mixture was cooled to room temperature, filtered to separate the catalyst, and then weighed. The reactants and products were analyzed by gas chromatograph and the products were also identified by gas chromatography mass spectomerty. The hydroperoxide in the reaction mixture was estimated by iodometric titration method. The GC analysis of reaction mixture showed 5.4% conversion of n-dodecane with 59.5% and 23.1% selectivity to dodecanones, dodecanols, respectively. Diketones are formed as side products with 7.9% selectivity.

EXAMPLE 11

A mixture of 5.0 g n-dodecane, 2.981 g TBHP in di-t-butylperoxide (DTBP), 0.25 g 5% Pd/C catalyst was charged to the glass reactor of 50 ml capacity fitted with a water condenser. The reaction was carried at 80° C. at atmospheric pressure under constant stirring for a period of 6 hours. The temperature was maintained by the use of circulated high temperature bath. At the end of the reaction, the reaction mixture was cooled to room temperature, filtered to separate the catalyst, and then weighed. The reactants and products were analyzed by gas chromatograph and the products were also identified by gas chromatography mass spectomerty. The hydroperoxide in the reaction mixture was estimated by iodometric titration method. The GC analysis of reaction mixture showed 9.6% conversion of n-dodecane with 58.3% and 22.8% selectivity to dodecanones, dodecanols, respectively. Diketones and acids are formed as side products with 5.6.% and 4.6% selectivity, respectively.

EXAMPLE 12

A mixture of 5.0 g n-dodecane, 2.981 g TBHP in di-t-butylperoxide (DTBP), 0.25 g 1% Pd/C catalyst was charged to the glass reactor of 50 ml capacity fitted with a water condenser. The reaction was carried at 80° C. at atmospheric pressure under constant stirring for a period of 6 hours. The temperature was maintained by the use of circulated high temperature bath. At the end of the reaction, the reaction mixture was cooled to room temperature, filtered to separate the catalyst, and then weighed. The reactants and products were analyzed by gas chromatograph and the products were also identified by gas chromatography mass spectometry. The hydroperoxide in the reaction mixture was estimated by iodometric titration method. The GC analysis of reaction mixture showed 9.3% conversion of n-dodecane with 54.0% and 28.7% selectivity to dodecanones, dodecanols, respectively. Diketones are formed as side products with 7.8% selectivity.

EXAMPLE 13

A mixture of 5.0 g n-dodecane, 2.984 g TBHP (in DTBP), 0.1 g 1% Pd/C catalyst was charged to the glass reactor of 50 ml capacity fitted with a water condenser. The reaction was carried at 80° C. at atmospheric pressure under constant stirring for a period of 6 hours. The temperature was maintained by the use of circulated high temperature bath. At the end of the reaction, the reaction mixture was cooled to room temperature, filtered to separate the catalyst, and then weighed. The reactants and products were analyzed by gas chromatograph and the products were also identified by gas chromatography mass spectometry. The hydroperoxide in the reaction mixture was estimated by iodometric titration method. The GC analysis of reaction mixture showed 7.4% conversion of n-dodeccne with 58.2% and 39.4% selectivity to dodecanones, dodecanols, respectively. Diketones are formed as side products with 6.0% selectivity.

EXAMPLE 14

A mixture of 5.0 g n-dodecane, 2.984 g TBHP (in DTBP), 0.5 g 5% Pd/C catalyst was charged to the glass reactor of 50 ml capacity fitted with a water condenser. The reaction was carried at 80° C. at atmospheric pressure under constant stirring for a period of 6 hours. The temperature was maintained by the use of circulated high temperature bath At the end of the reaction, the reaction mixture was cooled to room temperature, filtered to separate the catalyst, and then weighed. The reactants and products were analyzed by gas chromatograph and the products were also identified by gas chromatography mass spectometry. The hydroperoxide in the reaction mixture was estimated by iodometric titration method. The GC analysis of reaction mixture showed 9.9% conversion of n-dodecane with 53.2% and 29.4% selectivity to dodecanones, dodecanols, respectively, Diketones and acids are formed as side products with 7.5% and 4.5% selectivity, respectively,

EXAMPLE 15

A mixture of 5.0 g n-dodecane, 5.962 g TBHP (in DTBP) ($C_{12}$:TBHP mole ratio=1:2), 0.25 g 5% Pd/C catalysts was charged to the glass reactor of 50 ml capacity fitted with a water condenser. The reaction was carried at 80° C. at atmospheric pressure under constant stirring for a period of 6 hours. The temperature was maintained by the use of circulated high temperature bath. At the end of the reaction, the reaction mixture was cooled to room temperature, filtered to separate the catalyst, and then weighed. The reactants and products were analyzed by gas chromatograph and the products were also identified by gas chromatography mass spectometry. The hydroperoxide in the reaction mixture was estimated by iodometric titration method. The GC analysis of reaction mixture showed 11.9% conversion of n-dodecane with 62.2% and 23.1% selectivity to dodecanones, dodecanols, respectively. Diketones and acids are formed as side products with 5.9% and 3.2% selectivity, respectively.

EXAMPLE 16

A mixture of 5.0 g n-hexadecane, 2.498 g TBHP (in DTBP), 0.25 g 1% Pd/C catalyst was charged to the glass reactor of 50 ml capacity fitted with a water condenser. The reaction was carried at 80° C. at atmospheric pressure under constant stirring for a period of 6 hours. The temperature was maintained by the use of circulated high temperature bath. At the end of the reaction, the reaction mixture was cooled to room temperature, filtered to separate the catalyst, and then weighed. The reactants and products were analyzed by gas chromatograph and the products were also identified by gas chromatography mass spectometry. The hydroperoxide in the reaction mixture was estimated by iodometric titration method. The GC analysis of reaction mixture showed 8.4% conversion of hexadecane with 63.4% and 13.3% selectivity to hexadecanone, hexadecanols, respectively. Acids are formed as side products with 0.3% and % selectivity.

EXAMPLE 18

A mixture of 3.82 g TBHP in 4.255 g n-dodecane, 0.25 g 1% Pd/C catalyst was charged to the glass reactor of 50 ml capacity fitted with a water condenser. The reaction was carried at 80° C. at atmospheric pressure under constant stirring for a period of 6 hours. The temperature was maintained by the use of circulated high temperature bath. At the end of the reaction, the reaction mixture was cooled to room temperature, filtered to separate the catalyst, and then weighed. The reactants and products were analyzed by gas chromatograph and the products were also identified by gas chromatography mass spectometry. The hydroperoxide in the reaction mixture was estimated by iodometric titration method. The GC analysis of reaction mixture showed 14.6% conversion of n-dodecane with 57.0% and 30.5% selectivity to decanones, decanols, respectively. Diketones are formed as side products with 9.4% selectivity.

EXAMPLE 19

A mixture of 3.819 g TBHP in 4.253 g n-dodecane, 0.25 g 5% Pd/C catalyst was charged to the glass reactor of 50 ml capacity fitted with a water condenser. The reaction was carried at 80° C. at atmospheric pressure under constant stirring for a period of 6 hours. The temperature was maintained by the use of circulated high temperature bath. At the end of the reaction, the reaction mixture was cooled to room temperature, filtered to separate the catalyst, and then weighed. The reactants and products were analyzed by gas chromatograph and the products were also identified by gas chromatography mass spectometry. The hydroperoxide in the reaction mixture was estimated by iodometric titration method. The GC analysis of reaction mixture showed 16.4% conversion of n-dodecane with 54.4% and 19.1% selectivity to dodecanones, dodecanols, respectively. Diketones are formed as side products with 11.5% selectivity.

EXAMPLE 20

A mixture of 3.60 g TBHP in 4.349 g n-dodecane, 0.5 g 5% Pd/C catalyst was charged to the glass reactor of 50 ml capacity fitted with a water condenser. The reaction was carried at 80° C. at atmospheric pressure under constant stirring for a period of 6 hours. The temperature was maintained by the use of circulated high temperature bath. At the end of the reaction, the reaction mixture was cooled to room temperature, filtered to separate the catalyst, and then weighed. The reactants and products were analyzed by gas chromatograph and the products were also identified by gas chromatography mass spectometry. The hydroperoxide in the reaction mixture was estimated by iodometric titration method. The GC analysis of reaction mixture showed 15.8% conversion of n-dodecane with 40.7% and 17.7% selectivity to dodecanones, dodecanols, respectively. Diketones formed as side products with 10.1% selectivity.

EXAMPLE 21

A mixture of 5.0 g n-hexadecane, 2.498 g TBHP (in DTBP), 0.25 g 1% Pd/C catalysts was charged to the glass reactor of 50 ml capacity fitted with a water condenser. The reaction was carried at 80° C. at atmospheric pressure under constant stirring for a period of 6 hours. The temperature was maintained by the use of circulated high temperature bath. At the end of the reaction, the reaction mixture was cooled to room temperature, filtered to separate the catalyst, and then weighed. The reactants and products were analyzed by gas chromatograph and the products were also identified by gas chromatography mass spectometry. The hydroperoxide in the reaction mixture was estimated by iodometric titration method. The GC analysis of reaction mixture showed 8.4% conversion of hexadecane with 63.4% and 13.3% selectivity to hexadecanone, hexadecanols, respectively. Acids are formed as side products with 0.3% selectivity.

The Advantages of the Present Invention are
1. The present invention provides a process for the production of a mixture of alcohols and ketone by oxidation of higher alkanes using alkyl hydroperoxide as an oxidant at room or ambient temperature and atmospheric pressure conditions.
2. The present invention provides a process by the use of heterogeneous catalysts system, which can be separated from the reaction mixture and reused for the reaction.
3. The present invention provides a process that is environmentally more benign.
4. The invention produces ketones and alcohols as major products with high selectivity (60–90%).
5. The catalyst system reported in the present invention works at a lower temperature and hence the formation of carbon dioxide is negligible.

We claim:
1. A process for the preparation of a mixture of alcohols and ketones of higher alkanes selected from the group consisting of $C_8$–$C_{20}$ alkanes comprising subjecting the higher alkanes to liquid phase oxidation using a supported palladium catalyst system in the presence of alkyl hydroperoxide as an oxidant, cooling the reaction mixture to room temperature, and separating the products so obtained.
2. A process as claimed in claim 1 wherein the catalyst support is an inert solid support and is selected from the group consisting of alumina, silica and carbon.
3. A process as claimed in claim 2 wherein the catalyst support is carbon.
4. A process as claimed in claim 1 wherein the catalyst contains salts of palladium selected from the group consisting of acetates, bromides, chlorides, hydroxides, iodides, carbonates, nitrates, oxides, sulfides and propionates.
5. A process as claimed in claim 4 wherein the palladium salts are nitrates.
6. A process as claimed in claim 1 wherein the concentration of palladium in the catalyst is in the range of 0.3–10% by weight of the support.
7. A process as claimed in claim 1 wherein the mole ratio of the higher alkanes to palladium is in the range of 1–5000.
8. A process as claimed in claim 1 wherein the mole ratio of higher alkanes to the alkyl hydroperoxide is in the range of 0.1–5.0.
9. A process as claimed in claim 1 wherein the reaction is carried out at a temperature in the range of 10°–120° C.
10. A process as claimed in claim 1 wherein the reaction is conducted at atmospheric pressure in air or in an inert atmosphere.
11. A process as claimed in claim 1 wherein the liquid phase oxidation is carried out at a temperature in the range of 10°–120° C. and at atmospheric pressure for a period of 1–30 h.
12. A process as claimed in claim 1 wherein the reaction is carried out in a solvent selected from the group consisting of primary alcohol, alkyl nitrite and dialkyl ketone.
13. A process as claimed in claim 1 wherein the alkyl hydroperoxide is used as a solution in primary alcohols, alkanes, dialkyl peroxide or in an aromatic solvent.
14. A process as claimed in claim 1 wherein the products are separated by distillation.

* * * * *